(12) United States Patent
Klemm

(10) Patent No.: US 12,171,500 B2
(45) Date of Patent: Dec. 24, 2024

(54) LOCATING SYSTEM FOR MEDICAL DEVICES

(71) Applicant: Baxter Medical Systems GmbH + Co. KG, Saalfeld (DE)

(72) Inventor: Tobias Klemm, Saalfeld (DE)

(73) Assignee: Baxter Medical Systems GmbH & Co. KG, Saalfeld (DE)

( * ) Notice: Subject to any disclaimer, the term of this patent is extended or adjusted under 35 U.S.C. 154(b) by 654 days.

(21) Appl. No.: 17/335,419

(22) Filed: Jun. 1, 2021

(65) Prior Publication Data

US 2021/0378760 A1    Dec. 9, 2021

Related U.S. Application Data

(60) Provisional application No. 63/034,550, filed on Jun. 4, 2020.

(51) Int. Cl.
| | |
|---|---|
| A61B 34/20 | (2016.01) |
| G01B 11/00 | (2006.01) |
| G05B 19/402 | (2006.01) |
| G06T 7/70 | (2017.01) |
| G16H 40/20 | (2018.01) |
| A61B 90/00 | (2016.01) |

(52) U.S. Cl.
CPC ............ *A61B 34/20* (2016.02); *G01B 11/002* (2013.01); *G05B 19/402* (2013.01); *G06T 7/70* (2017.01); *G16H 40/20* (2018.01); *A61B 2034/2055* (2016.02); *A61B 2090/3937* (2016.02); *G05B 2219/45169* (2013.01); *G06T 2207/30204* (2013.01)

(58) Field of Classification Search
CPC ............ A61B 34/20; A61B 2034/2055; A61B 2090/3937; G01B 11/002; G05B 19/402; G05B 2219/45169; G06T 7/70; G06T 2207/30204; G16H 40/20
See application file for complete search history.

(56) References Cited

U.S. PATENT DOCUMENTS

| | | | |
|---|---|---|---|
| 6,591,239 B1 | 7/2003 | McCall et al. | |
| 9,400,170 B2 | 7/2016 | Steffey | |
| 2012/0078236 A1* | 3/2012 | Schoepp | A61B 5/061 606/1 |
| 2014/0171787 A1* | 6/2014 | Garbey | A61B 5/061 600/424 |
| 2015/0216746 A1 | 8/2015 | Dirauf et al. | |

(Continued)

FOREIGN PATENT DOCUMENTS

| | | |
|---|---|---|
| CN | 102047256 A | 5/2011 |
| CN | 104814847 A | 8/2015 |

(Continued)

*Primary Examiner* — Phuong H Nguyen
(74) *Attorney, Agent, or Firm* — Price Heneveld LLP

(57) ABSTRACT

A locating system for a surgical suite includes optical markers coupled to a medical device. A sensor is configured to obtain an initial position data of the optical markers. A laser device is configured to obtain subsequent position data of the optical markers. A controller receives the initial position data from the sensor and the subsequent position data from the laser device. The controller is configured to determine a position of the medical device within the surgical suite and recognize a type of the medical device in response to the optical markers.

18 Claims, 5 Drawing Sheets

(56) References Cited

U.S. PATENT DOCUMENTS

| | | |
|---|---|---|
| 2015/0374452 A1 | 12/2015 | Saito |
| 2017/0054954 A1 | 2/2017 | Keitler et al. |
| 2019/0060026 A1 | 2/2019 | Geerlings et al. |
| 2019/0121522 A1 | 4/2019 | Davis et al. |
| 2019/0192874 A1 | 6/2019 | Shukla |
| 2019/0321126 A1 | 10/2019 | Otto et al. |
| 2020/0008878 A1* | 1/2020 | Srimohanarajah ..... A61B 90/39 |
| 2020/0019231 A1 | 1/2020 | Chung et al. |
| 2020/0193622 A1* | 6/2020 | Stopp .................... A61B 34/20 |
| 2020/0219604 A1 | 7/2020 | Hallack et al. |
| 2020/0333428 A1* | 10/2020 | Sun .......................... G01S 5/16 |
| 2020/0337777 A1* | 10/2020 | Liu ....................... G16H 15/00 |

FOREIGN PATENT DOCUMENTS

| | | | |
|---|---|---|---|
| CN | 106102647 A | 11/2016 | |
| CN | 108778179 A | 11/2018 | |
| DE | 102019004233 A1 | 12/2019 | |
| EP | 1952778 A1 | 8/2008 | |
| EP | 2512342 B1 | 9/2016 | |
| EP | 3506291 A1 | 7/2019 | |
| WO | 2009151535 A1 | 12/2009 | |
| WO | 2017100124 A1 | 6/2017 | |
| WO | 2017147596 A1 | 8/2017 | |

* cited by examiner

LOCATING SYSTEM FOR MEDICAL DEVICES

CROSS-REFERENCE TO RELATED APPLICATION

This application claims priority to and the benefit under 35 U.S.C. § 119(e) of U.S. Provisional Application No. 63/034,550, filed on Jun. 4, 2020, entitled "LOCATING SYSTEM FOR MEDICAL DEVICES," the disclosure of which is hereby incorporated herein by reference in its entirety.

FIELD OF THE DISCLOSURE

The present disclosure generally relates to a locating system for medical devices in a surgical suite.

SUMMARY OF THE DISCLOSURE

According to one aspect of the present disclosure, a locating system for a surgical suite includes optical markers coupled to a medical device. A sensor is configured to obtain initial position data of the optical markers. A laser device is configured to obtain subsequent position data of the optical markers. A controller is configured to receive the initial position data from the sensor and the subsequent position data from the laser device. The controller is configured to determine a position of the medical device within said surgical suite and recognize a type of the medical device in response to the optical markers.

According to another aspect of the present disclosure, a method of adjusting a device within a surgical suite includes detecting a type of a medical device within said surgical suite and determining whether the medical device is a fixed device or a movable device. A position of the medical device is detected using a sensor and at least one optical marker coupled to the medical device. At least one of a movement path and an adjustment path for the medical device is determined. The medical device is moved within said surgical suite in response to a detected position of the medical device.

According to another aspect of the present disclosure, a locating system for a surgical suite includes a plurality of optical markers coupled to a medical device. A sensor is configured to obtain initial position data of the plurality of optical markers. A laser device is configured to obtain subsequent position data of the plurality of optical markers. A controller is configured to receive the initial position data from the sensor and the subsequent position data from the laser device. The controller is configured to determine a position of the medical device within said surgical suite. An adjustment feature is coupled to the medical device and is communicatively coupled to the controller. The adjustment feature is configured to adjust the medical device along at least one of a movement path and an adjustment path in response to a signal from the controller.

These and other features, advantages, and objects of the present disclosure will be further understood and appreciated by those skilled in the art by reference to the following specification, claims, and appended drawings.

DETAILED DESCRIPTION

Figure 1:
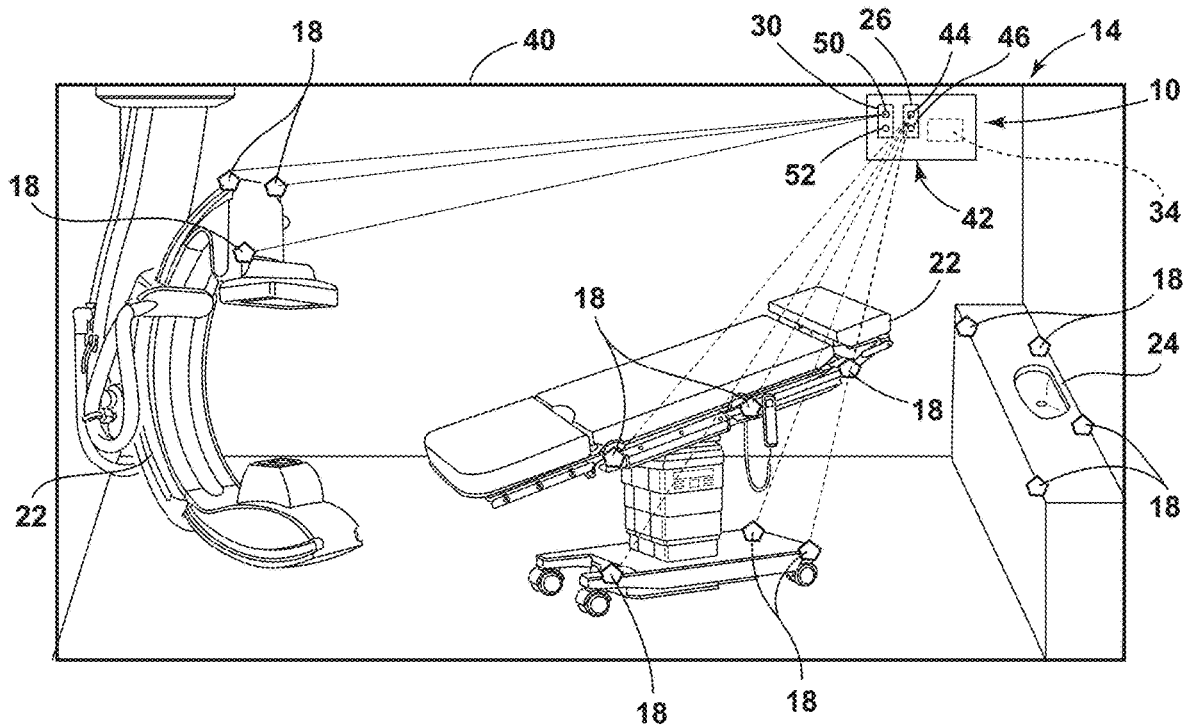
FIG. 1 is a schematic view of a surgical suite that includes a locating system, according to the present disclosure.

The present illustrated embodiments reside primarily in combinations of method steps and apparatus components related to a locating system for medical devices. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-6, reference numeral 10 generally designates a locating system for a surgical suite 14. Optical markers 18 are coupled to a medical device, which may be a movable device 22 or a fixed device or structure 24. A three-dimensional (3D) sensor 26 is configured to obtain initial position data of the optical markers 18. A laser device 30 is configured to obtain confirmation or subsequent position data of the optical markers 18. A controller 34 receives the initial position data from the 3D sensor 26 and the subsequent position data from the laser device 30. The controller 34 is configured to determine a position of the movable device 22 within the surgical suite 14 and to control movement of the movable device 22 in response to the initial position data and the subsequent position data. The controller 34 is also configured to recognize a type of the movable device 22 and the fixed device 24 in response to the optical markers 18.

Figure 2:
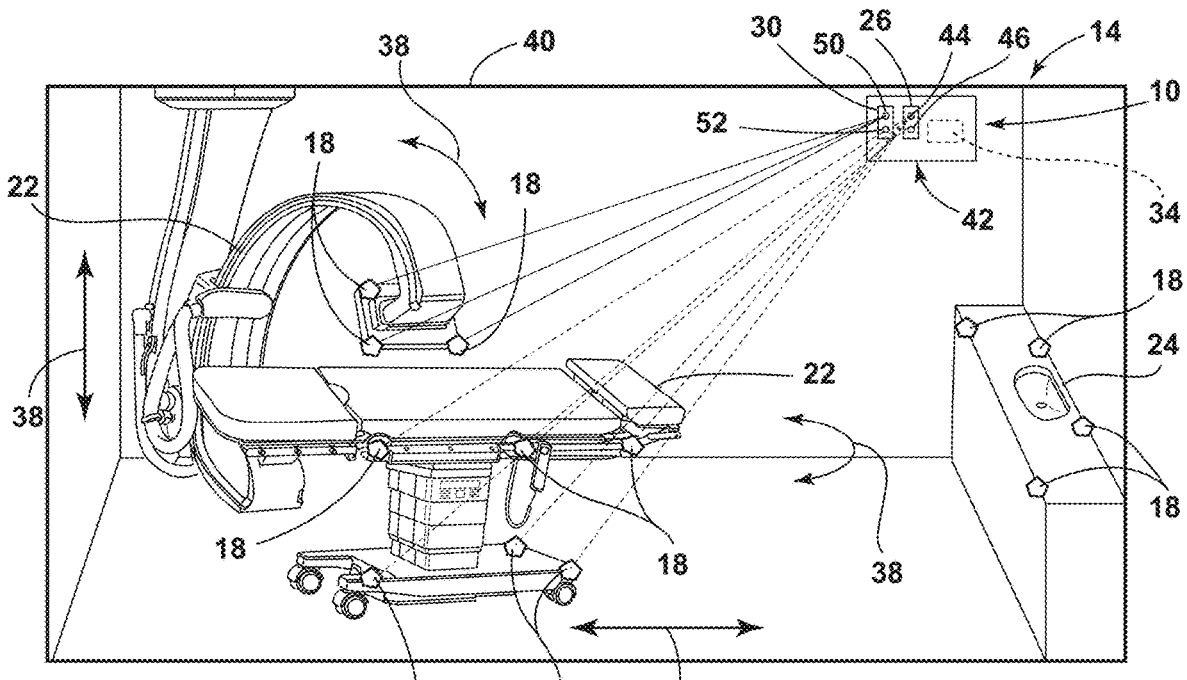
FIG. 2 is a schematic view of the surgical suite of FIG. 1 with medical devices located in different positions.

Referring to FIGS. 1 and 2, the locating system 10 is illustrated within the surgical suite 14 but may be used in other medical settings and/or environments. The locating system 10 is generally configured to determine a position of the movable device 22 within the surgical suite 14 and control the movement of the movable device 22. The surgical suite 14 may include one or more movable devices 22 and fixed devices or structure 24 at any given time. The medical devices and structures 22, 24 may be any static or dynamic equipment commonly found within a surgical suite 14, used for medical procedures, or otherwise used within a medical environment.

As illustrated in FIG. 1, the surgical suite 14 includes a counter adjacent to one wall, which is an example of one fixed structure 24 within the surgical suite 14. The illustrated surgical suite 14 also includes two examples of different types of movable devices 22. The exemplary movable devices illustrated in FIG. 1 are a surgical table and a C-arm X-ray machine. The surgical table may be freely moved about the surgical suite 14 from one physical position to another along a movement path 36. The C-arm X-ray machine is fixedly coupled to a ceiling 40 within the surgical suite 14 and therefore may not freely move between different physical locations within the surgical suite 14 (e.g., left to right or front to back). However, the C-arm X-ray machine may be freely adjusted, such as in height or rotation, while remaining in the fixed location. Accordingly, the C-arm X-ray machine is generally movable along an adjustment path 38.

Some movable devices 22, for example the surgical table, may move along the movement path 36 and the adjustment path 38. The movement path 36 generally defines a space between two distinct or discrete physical locations (e.g., moving horizontally about the surgical suite 14). The adjustment path 38 generally defines a change between physical states, conditions, or characteristics at a single physical location or between physical locations as the movable device 22 translates along the movement path 36. Other examples of the medical device or structure 22, 24 may be, for example, instrument tables, a computer or other electronic devices, storage features, imaging machines, and/or any other equipment.

The optical markers 18 are generally coupled to an outer surface of each movable device 22 and fixed device or structure 24 within the surgical suite 14. The optical markers 18 may be any practicable feature that can be recognized by the locating system 10. The optical markers 18 enable optical registration and measurement of each movable device 22. The number of optical markers 18 may differ based on the size, geometry, type of the movable device 22 or the fixed device 24, the static or dynamic nature of the movable device 22 or the fixed device 24, whether the movable device 22 translates along the movement path 36, or whether the movable device 22 is moved along the adjustment path 38, as well as various aspects of the movable device 22. For example, as illustrated in FIG. 1, the fixed C-arm X-ray machine includes three optical markers 18, the surgical table includes six optical markers 18, and the counter includes four optical markers 18. The number of optical markers 18 on the illustrated devices and structures 22, 24 is merely exemplary, and any practicable number of optical markers 18 may be coupled to each device or structure 22, 24 without departing from the teachings herein.

As illustrated in FIG. 1, a locating assembly 42 is coupled to the ceiling 40 within the surgical suite 14. The locating assembly 42 may include the 3D sensor 26, the laser device 30, and the controller 34. Positioning the locating assembly 42 adjacent to or on the ceiling 40 may increase the area within the surgical suite 14 that the 3D sensor 26 and the laser device 30 can obtain data from and consequently increase the number of movable devices 22 that the locating system 10 can control. However, it is contemplated that the locating assembly 42 may be disposed in any practicable location or in multiple locations within the surgical suite 14. Each of the 3D sensor 26, the laser device 30, and the controller 34 may be included in a single component, or alternatively, may be separate components within the surgical suite 14.

Figure 4:
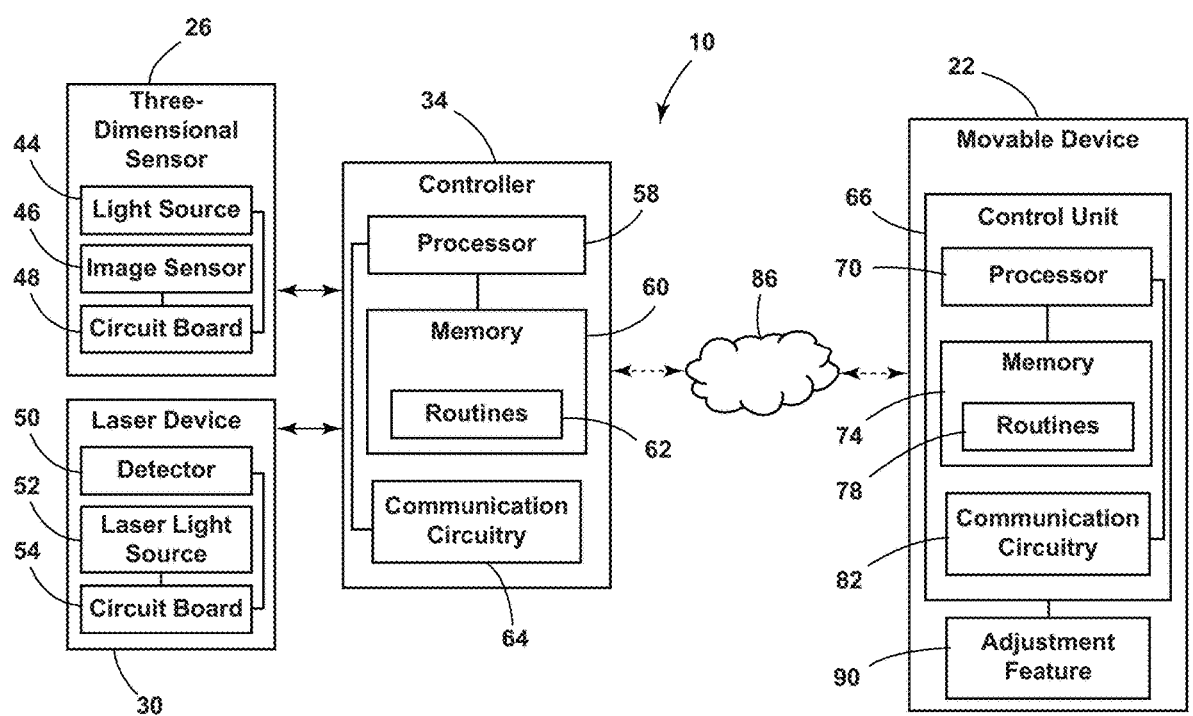
FIG. 4 is a box diagram of a locating system in communication with a medical device, according to the present disclosure.

The locating system 10 is configured to detect the position of the movable devices 22 and the fixed devices 24 within the surgical suite 14 and recognize each type of device or structure 22, 24. The 3D sensor 26 of the locating system 10 is configured to obtain the initial position data of the optical markers 18. The 3D sensor 26 measures a distance between the 3D sensor 26 and the optical markers 18. The 3D sensor 26 generally includes a light source 44, an image sensor 46, and a circuit board 48 (FIG. 4). The light source 44 of the 3D sensor 26 is configured to emit light in the visible or invisible spectrum into the surgical suite 14. The emitted light is generally reflected by each optical marker 18 and is subsequently detected by the image sensor 46.

The 3D sensor 26 is configured to measure the distance between the 3D sensor 26 and each optical marker 18. Consequently, the 3D sensor 26 is configured to measure a distance between the movable device 22 or the fixed device 24 having the optical markers 18 and the 3D sensor 26 based on a time difference between the emission of light and the return of the reflected light to the 3D sensor 26. The 3D sensor 26 may use any practicable method of determining the distance between the 3D sensor 26 and the movable device 22 or the fixed device 24, such as, for example, timed pulses of light, phase shifts of the reflected light, or any combination thereof. For example, the locating system 10 may use time-of-flight calculations generally associated with laser tracking devices. Such devices calculate distance based on time-of-flight and position based on the angular orientation or rotational and elevation axes that identify the projection line of the laser. In another example, the locating system 10 may be configured as an optical vision system that uses the parallax effect of stereoscopic cameras to determine position and depth.

The light source 44 of the 3D sensor 26 may be any type of light source. In specific non-limiting examples, the 3D sensor 26 may include a laser light or a light-emitting diode (LED). Generally, the 3D sensor 26 is configured to emit infrared light (e.g., having a wavelength in a range between about 700 nm and about 1 mm), near-infrared light (e.g., having a wavelength in a range between about 700 nm and about 940 nm), or a combination thereof.

In non-limiting examples, the 3D sensor 26 may be a time-of-flight camera. In such examples, the 3D sensor 26 is configured to determine a distance between the 3D sensor 26 and the movable device 22 based on the difference in time between the emission of light from the light source 44 and the reception of reflected light back to the image sensor 46 of the 3D sensor 26. More specifically, the time between the initiation of the light by the light source 44 of the 3D sensor 26 and the reception of the reflected light received by the image sensor 46 is indicative of the distance between the 3D sensor 26 and the movable device 22 or the fixed device 24.

The distance and position determined by the 3D sensor 26 may be communicated to the controller 34 as the initial position data. The 3D sensor 26 may continue to obtain the initial position data of the movable devices 22 as the movable devices 22 translate along the movement path 36 or the adjustment path 38 to dynamically calibrate and update the position of the movable devices 22.

The 3D sensor 26 may also be configured to obtain identification data regarding the type of movable device 22 or fixed device 24 based on the arrangement or pattern of the optical markers 18. Accordingly, the locating system 10 may recognize the type of movable devices 22 or fixed devices 24 within the surgical suite 14, as well as the position of each device 22, 24. The optical markers 18 may be arranged in a specific pattern that is representative of a particular code that corresponds to the type of device 22, 24 registered or stored within the controller 34. Additionally or alternatively, the optical markers 18 may be arranged to reflect the light emitted from the 3D sensor 26 in a specific manner or have other distinctive properties that the locating system 10 recognizes. The 3D sensor 26 may obtain the identification data relating to the type of device 22, 24 and communicate the identification data to the controller 34. Recognizing the type of device or structure 22, 24 may be advantageous for the locating system 10 to determine the exact position and arrangement of the movable devices 22 and the fixed devices 24 within the surgical suite 14, as well as determine if the detected devices 22, 24 are movable or fixed.

Referring still to FIGS. 1 and 2, the laser device 30 of the locating assembly 42 is configured to obtain confirmation or subsequent position data of each optical marker 18 disposed on the movable devices 22. The laser device 30 may be used by the locating system 10 to determine a more precise and/or more accurate position of the optical markers 18 relative to the initial position determined by the 3D sensor 26. The accuracy of the laser device 30 may be proportional to the distance between the laser device 30 and the optical markers 18. In a specific non-limiting example, the laser device 30 may provide position accuracies of approximately 0.1 mm/m. Accordingly, the laser device 30 may confirm and enhance the accuracy of the initial position data obtained by the 3D sensor 26.

The laser device 30 may detect each optical marker 18 using, for example, triangulation, pulse modulation, or a combination thereof. Angle calculations may be utilized to determine the distance between the laser device 30 and each optical marker 18. The laser device 30 may include an imager (e.g., a complementary metal-oxide-semiconductor or a charge-coupled device) or a detector 50 (e.g., a position sensitive detector), as well as a laser light source 52 and a circuit board 54 (FIG. 4). The laser light source 52 generally emits infrared and/or near-infrared light. The laser light source 52 may emit light into the surgical suite 14 and reflected light from the optical markers 18 may be received through focusing optics and directed into the detector 50 of the laser device 30. As the movable devices 22 are moved within the surgical suite 14, the reflected light moves relative to the imager or detector 50, and the laser device 30 may continue to obtain the confirmation or subsequent position data as the movable devices 22 translate along the movement path 36 or the adjustment path 38.

The initial position data obtained by the 3D sensor 26 may provide a rough estimate of the position of the optical markers 18 within the surgical suite 14. The initial position data may be communicated to the controller 34 and subsequently communicated to the laser device 30. The laser device 30 may utilize the initial position data to direct the laser light into the general area of the optical markers 18 as determined by the 3D sensor 26. The information obtained by the 3D sensor 26 may guide the area for the laser device 30 to scan or pinpoint a location for the laser device 30 to direct the laser light to obtain a precise position of each optical marker 18.

The movable device 22 within the surgical suite 14 may be located by the controller 34 in an absolute or relative coordinate system. As previously discussed, the location of the movable devices 22 is calculated by the controller 34 based on positional information identified by the 3D sensor 26 in combination with the measurements from the laser device 30. In operation, the laser light emitted from the laser device 30 is reflected from the optical markers 18, which may be implemented as retro-reflective targets or similar reflective targets. The controller 34 detects or improves the calculated position of each of the movable devices 22 based on the angular orientation (azimuth axis and elevation axis) and distance readings measured by the laser device 30 in order to accurately determine the positions and/or orientations of the movable devices 22 in the surgical suite 14. The controller 34 may identify the positions of the movable devices 22 in relation to one another, the fixed devices 24, and/or based on their associated positions within a calibrated coordinate grid and operating envelope of the surgical suite 14. The operating envelope may be defined or programmed into the controller 34 as a predetermined working range defined in relation to the coordinate grid.

According to various aspects, the light emitted by the light source 44 of the 3D sensor 26 may be scattered by bright surfaces or can produce distorted reflections based on the shape of the reflecting surface, which can affect the distance measurement obtained by the 3D sensor 26. The laser device 30 may be advantageous for use with highly reflective surfaces, such as metallic components, which are common within the surgical suite 14. Accordingly, the 3D sensor 26 may provide an estimated position of the optical markers 18 and provide dynamic calibration for the locating system 10, and the laser device 30 can confirm the exact positioning of each optical marker 18.

Figure 3:
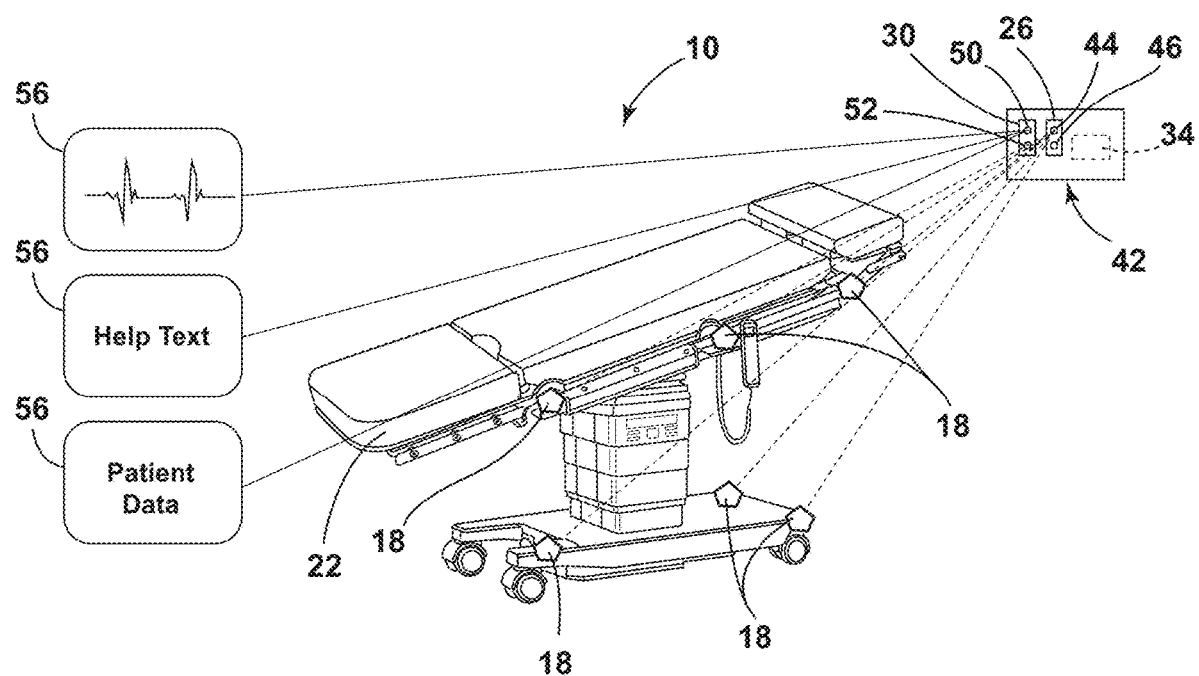
FIG. 3 is a schematic view of a locating system for a surgical suite, according to the present disclosure.

Referring to FIG. 3, as previously noted, the laser device 30 may obtain subsequent position data of the optical markers 18, which may be utilized to confirm the position of the movable devices 22 or the fixed devices 24 within the surgical suite 14. Additionally, the laser device 30 may be configured to project information 56 onto a surface within the surgical suite 14. The surface may be any surface within the surgical suite 14, such as, for example, a wall, a floor space, a whiteboard, or a removable or permanent feature for displaying data. The laser device 30 may project the information 56 on any surface with spatial alignment and without substantial distortion of the information 56. The information 56 can be or include any information or data that may be useful within the surgical suite 14 or for a medical procedure.

For example, the projected information 56 may be data about the movable devices 22 or the fixed devices 24 (e.g., device data, type of device data, etc.), information about the movement path 36 or the adjustment path 38 (e.g., device movement data, obstruction data, etc.), information 56 output from the movable devices 22 or the fixed devices 24 (e.g., sensed patient data, device position data, etc.), information 56 about the patient (e.g., stored patient data, patient record data, etc.), or any other information 56. Different types of information 56 may also be projected and displayed simultaneously, as illustrated in FIG. 3. The information 56 may be displayed as a static image or a moving image. The laser device 30 may operate to obtain the subsequent position data of the optical markers 18 independently of and simultaneously with the projection of the information 56.

Referring to FIG. 4, the locating system 10 includes the controller 34, which includes a processor 58, a memory 60, and other control circuitry. Instructions or routines 62 are stored within the memory 60 and executable by the processor 58. The controller 34 may include at least one routine 62 that relates to receiving the initial position data from the 3D sensor 26 and determining an initial position of each optical marker 18 (FIG. 1) based on the initial position data. Similarly, the controller 34 may include at least one routine 62 that relates to receiving the subsequent position data from the laser device 30 and confirming the position of each optical marker 18 based on the subsequent position data. Additionally or alternatively, the controller 34 may include at least one routine 62 related to adjusting the laser device 30 in response to the initial position data to emit the light toward the general position of the optical markers 18.

According to various aspects, the controller 34 may store information regarding registered movable devices 22 or fixed devices 24 in the memory 60. The controller 34 may include at least one routine 62 configured to evaluate the pattern or code of the optical markers 18 and recognize the type of device or structure 22, 24 using the stored registered movable devices 22 and fixed devices 24. The controller 34 may store physical characteristics, including footprint, volume, geometry, etc. of each registered device or structure 22, 24. The controller 34 may also store information within the memory 60 relating to the geometry of the surgical suite 14, as well as information regarding the position of the fixed devices or structures 24 within the surgical suite 14 that may act as obstacles. Clearance or interference zones for each to the registered devices or structures 22, 24 that identify the locations obstructed or occupied by each of the devices 22, 24 relative to the optical markers 18 may be programmed into the controller 34. These parameters may be accessed with the identification data.

As previously noted, the position of each movable device 22 may be obtained through the initial position data obtained by the 3D sensor 26 and enhanced or verified with the subsequent position data obtained by the laser device 30. Additionally or alternatively, as a safety redundancy or a collision prevention protocol, the position of the fixed devices or structure 24 may be verified with the initial position data obtained by the 3D sensor 26 and/or verified with the subsequent position data obtained by the laser device 30. While the position and physical characteristics of the fixed devices 24 are generally stored within the memory 60 of the controller 34, the position or physical characteristic may be confirmed as part of a protocol before a movable device 22 is translated along the movement path 36 or the adjustment path 38.

The controller 34 may include communication circuitry 64 to allow the controller 34 of the locating system 10 to communicate with one or more of the movable devices 22. One, some, or all of the movable devices 22 within the surgical suite 14 may include a control unit 66 that has a processor 70, a memory 74, and other control circuitry. Instructions or routines 78 are stored in the memory 74 and executable by the processor 70. The movable devices 22 may include communication circuitry 82 to allow communication with the controller 34. The controller 34 is generally configured for gathering inputs from the 3D sensor 26 and the laser device 30, processing the inputs, and generating an output response to the input. The controller 34 may send a signal to the movable device 22 to control the movement of the movable device 22 within the surgical suite 14.

The controller 34 and the control unit 66 disclosed herein may include various types of control circuitry, digital or analog, and may include the processors 58, 70, a microcontroller, an application specific circuit (ASIC), or other circuitry configured to perform the various input or output, control, analysis, or other functions described herein. The memories 60, 74 described herein may be implemented in a variety of volatile and nonvolatile memory formats. The routines 62, 78 include operating instructions to enable various methods and functions described herein.

The controller 34 and the control unit 66 are communicatively coupled with one another to establish a communication interface 86 between the locating system 10 and each movable device 22. The controller 34 may also be configured to communicate with remote servers (e.g., cloud servers, Internet-connected databases, computers, etc.) via the communication interface 86. The communication interface 86 may be a network, which may be one or more various communication mechanisms, including any combination of wired (e.g., cable and fiber) and/or wireless communications and any network topology or topologies.

Exemplary networks include wireless communication networks, such as, for example, a Wi-Fi transceiver, an IrDA transceiver, an RFID transceiver, etc. Additionally or alternatively, the communication interface 86 may be implemented via one or more direct or indirect nonhierarchical communication protocols, including but not limited to, Bluetooth®, Bluetooth® low energy (BLE), Thread, Ultra-Wideband, Z-wave, ZigBee, etc. In examples where the controller 34 and the control unit 66 communicate via a Bluetooth® device, the movable device 22 and the locating system 10 may be linked or synchronized. It is generally contemplated that the locating system 10 may be associated or synced with any number of movable devices 22. Each of the controller 34 and the control unit 66 may include circuitry configured for bidirectional wireless communication.

Additionally, the exemplary networks can include, but are not limited to, global system for mobile communication (GSM), general packet radio services, code division multiple access, enhanced data GSM environment, fourth generation (4G) wireless, fifth generation (5G) wireless, Wi-Fi, world interoperability for wired microwave access (WiMAX), local area networks (LAN), wide area networks (WAN), including the Internet and other data communication services. It is contemplated that the controller 34 and the control unit 66 can communicate by any suitable technology for exchanging data. By flexibly implementing the communication interface 86, various devices and servers may communicate with one another directly via the wireless communication interface 86 or a cellular data connection.

Figure 5:
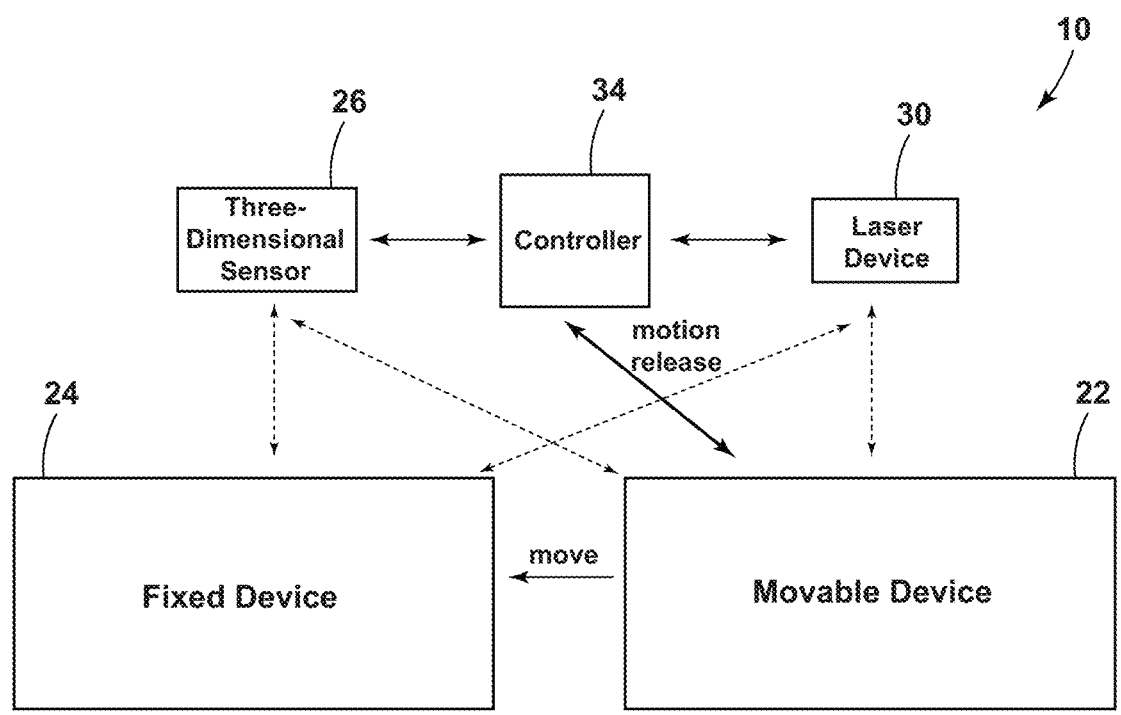
FIG. 5 is a flow diagram of a locating system for controlling movement of a medical device within a surgical suite, according to the present disclosure.

Referring to FIGS. 2, 4, and 5, the communication interface 86 between the controller 34 of the locating system 10 and the control unit 66 of the movable device 22 may be used for transmission of signals to control the movement of one or more of the movable devices 22 along one or both of the movement path 36 and the adjustment path 38. Each movable device 22 may include an adjustment feature 90. The adjustment feature 90 may be any assembly or system that adjusts a physical position or a characteristic of the movable device 22. Characteristics of the movable device 22 that may be adjusted may be, for example, an angle, a height, an orientation, a physical location, or any other aspect of the movable device 22 (e.g., trend, tilt, maximum stroke, etc.).

The adjustment feature 90 may assist in translation and steering of a surgical table or other support apparatus. In a non-limiting example, the adjustment feature 90 may be a motorized wheel assembly that translates the movable device 22 along the movement path 36 to a different physical position within the surgical suite 14. In another non-limiting example, the adjustment feature 90 may be a hydraulic or pneumatic cylinder, a motorized assembly, etc. that adjusts a height-based characteristic of the movable device 22 along the adjustment path 38. For example, the adjustment feature 90 may be a hydraulic adjustment for a surgical table or other support apparatus. Additionally or alternatively, the adjustment feature 90 may be an articulating robotic arm with one or more degrees of freedom. Other non-limiting adjustment features 90 may include gear assemblies or rail assemblies. The configuration of the adjustment feature 90 generally depends on the movable device 22.

In operation, it is contemplated that the locating system 10 may detect a position of each movable device 22 and fixed device 24 within the surgical suite 14, recognize the type of movable device 22 and fixed device 24, and control movement of at least one of the movable devices 22. The 3D sensor 26 may determine the distance between the 3D sensor 26 and each of the movable devices 22 using each optical marker 18 (FIG. 1), as well as a rough position of each optical marker 18. The laser device 30 may confirm the distance between each of the movable devices 22 and the laser device 30 using each optical marker 18. Accordingly, using the 3D sensor 26 and the laser device 30, the locating system 10 may detect the precise position of each movable device 22 within the surgical suite 14.

Additionally, as previously noted, the locating system 10 may independently or simultaneously determine the type of devices or structures 22, 24 within the surgical suite 14. The 3D sensor 26 may obtain identification data relating to the type of movable device 22 based on the arrangement of the optical markers 18. It is contemplated that the optical markers 18 may have different properties that can be detected by the 3D sensor 26 or the controller 34 indicative of the type of movable device 22 or fixed device 24.

The controller 34 may include at least one routine 62 that determines the position of each movable device 22 within the surgical suite 14 in response to the initial and subsequent position data received. The controller 34 may include stored information regarding the position of the fixed devices 24 and physical characteristics, such as geometries, of each type of movable device 22 and fixed device 24. Using the identification data in conjunction with the initial and subsequent position data, the controller 34 may also determine the precise orientation of each movable device 22 within the surgical suite 14. The orientation, precise position, and type of each movable device 22 and fixed device 24 may be utilized by the controller 34 to determine the movement path 36 or the adjustment path 38.

The controller 34 may send a signal to the control unit 66 of each movable device 22 to be moved. It is contemplated that one, several, or all of the devices 24 within the surgical suite 14 may include the control unit 66 to directly communicate with the controller 34. Alternatively, the fixed devices 24 may be free of direct communication with the controller 34, while the movable devices 22 may include the control unit 66 for communicating with the controller 34. As previously noted, the movable devices 22 may be freely movable about the surgical suite 14 (e.g., movable between different physical positions) along the movement path 36. Additionally or alternatively, the movable devices 22 may also have adjustable characteristics (e.g., height, tilt, rotation, etc.) and may move along the adjustment path 38 between different conditions or states. It is contemplated that the movable medical devices 22 may be manually or automatically movable. Each of the movement path 36 and the adjustment path 38 may be determined to avoid collisions with other movable devices 22 and fixed devices 24 within the surgical suite 14.

The controller 34 is configured to communicate at least one of the movement path 36 or the adjustment path 38 to the movable device 22 based on initial and subsequent position data received from the 3D sensor 26 and the laser device 30 of each recognized device or structure, the type of movable device 22, and the stored physical characteristics of the surgical suite 14 and the movable device 22. Accordingly, the controller 34 directs the movable device 22 to a new physical position within the surgical suite 14 while avoiding other objects (e.g., movable devices 22 and fixed devices 24) within the surgical suite 14. More specifically, the controller 34 may control the movement of the movable devices 22 in a manner that avoids collisions with other detected devices or structures 22, 24. This may be accomplished by programming clearance or interference zones for each of the devices 22, 24 that identify the locations obstructed or occupied by each of the objects relative to the optical markers 18. These parameters may be accessed with the identification data.

Additionally or alternatively, the controller 34 may direct the movable device 22 to move along the adjustment path 38 to a new setting or state in a manner that avoids collisions with other movable devices 22 and the fixed devices 24. As such, some or all of the movable devices 22 within the surgical suite 14 may be automatically moved within the surgical suite 14. It is also contemplated that the control unit 66 of the movable device 22 may determine the movement path 36 or the adjustment path 38 based on information received from the controller 34. Accordingly, the signal from the controller 34 may operate as a movement release signal to activate independent movement of the movable device 22.

Using the information from the 3D sensor 26 and the laser device 30, the controller 34 may determine the position and orientation of each movable device 22 and fixed device 24 within the surgical suite 14. The precise orientation of the devices 22, 24 may be determined using at least one of the position of the optical markers 18 as well as stored information about the devices 22, 24. Using other sensed or stored information about the surgical suite, the controller 34 is configured to determine the movement path 36 or the adjustment path 38 to move or adjust the movable devices 22 based on a selected triggering event. The selected triggering event may be a user input, an event (e.g., overhead light activation or caregiver log-in), etc. The controller 34 may store the subsequent position for each device 22 that corresponds with the triggering event.

For example, the controller 34 may store information that when the overhead light is activated in the surgical suite 14, the support apparatus is to be positioned directly under the overhead light. If the surgical table is not in the correct position, the controller 34 may automatically adjust the position of the support apparatus. In another non-limiting example, the C-arm x-ray machine may be adjusted to provide imaging of the patient on the support apparatus in response to an input from a medical professional in the surgical suite 14. The medical professional may issue a command through a user interface (e.g., a touch command, a voice command, a gesture, etc.) that is communicated to the locating system 10. The locating system 10 may then adjust the C-arm x-ray machine in accordance with the command.

Based on the triggering event, the controller 34 is configured to determine or map the movement path 36 or the adjustment path 38 to adjust the movable device 22 to the selected subsequent position or orientation. The controller 34 obtains the position information of the various movable and fixed devices 22, 24 within the surgical suite 14. Using the selected subsequent or end location or position and the position and orientation of other devices 22, 24 within the surgical suite 14, the controller 34 determines an appropriate movement path 36 or adjustment path 38 that avoids other devices 22, 24 within the surgical suite 14. The controller 34 may then send a signal to the control unit 66 of the movable device 22, which consequently activates the adjustment feature 90 to move the movable device 22.

It is contemplated that additional optical markers 18 may be included on surfaces of the surgical suite 14 (e.g., walls) to verify stored information of the surgical suite. Additionally or alternatively, it is contemplated that the medical professionals in the surgical suite 14 may wear or otherwise have optical markers 18 that can be sensed by the locating system 10. Such configurations may be advantageous for moving the movable devices 24 around the medical professionals.

Figure 6:
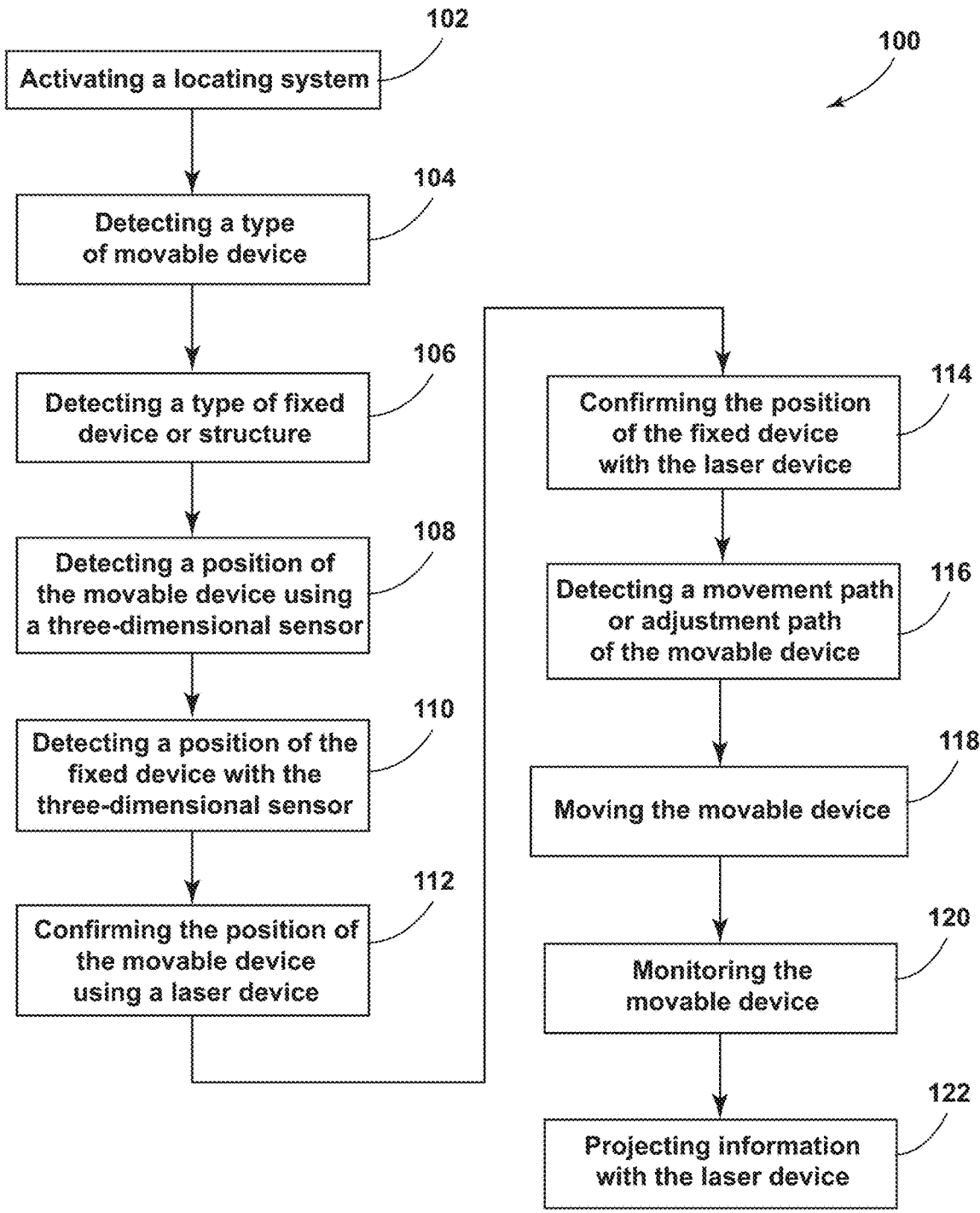
FIG. 6 is a flow diagram of a method for adjusting a medical device along a movement path or an adjustment path, according to the present disclosure.

Referring to FIG. 6, and with further reference to FIGS. 1-5, a method 100 of adjusting the movable devices 22 in the surgical suite 14 includes step 102 of activating the locating system 10. The locating assembly 42 may be activated in response to the triggering event. The locating assembly 42 may be activated through an automatic or automated process or through a manual input. The triggering event may indicate the movable devices 22 to be moved and the subsequent or end position of the movable device 22.

In step 104, the type of movable devices 22 is detected by the locating assembly 42. The 3D sensor 26 may obtain identification data regarding the type of the movable devices 22 based on the arrangement or pattern of the optical markers 18 on the selected movable device 22, which may subsequently be communicated to the controller 34. The 3D sensor 26 may be utilized to sense or detect the position or arrangement of the optical markers 18 around the surgical suite 14. The controller 34 may include stored information in the memory 60 regarding the arrangement of the optical markers 18, which associates specific patterns with certain types of devices or structures. Using the specific patterns, the controller 34 may determine that the device 22 is a movable device 22.

Further, in step 104, the controller 34 may correlate the detected type of device 22 with stored characteristics. Knowing the type of movable device 22 may be advantageous for ascertaining whether one or more movement paths 36, one or more adjustment paths 38, or both are available to the movable device 22. For example, when the controller 34 determines that the movable device 22 is the support apparatus, the controller 34 may recognize a size, shape, ability to move, ability to adjust, etc.

In step 106, the controller 34 may also detect the type of additional devices in the surgical suite, including the fixed devices 24 and other movable devices 22 (e.g., those not selected to be moved), using the 3D sensor 26 and the additional optical markers 18 coupled to the additional devices. The controller 34 may then correlate the type of device 22, 24 with stored characteristics. For example, when the controller 34 determines that the fixed device 24 is the countertop, the controller 34 may recognize a size, shape, interference zone, position in the surgical suite 14, etc. Using the specific patterns of the optical markers 18, the controller 34 may determine that the device 22, 24 is fixed or movable. Accordingly, using the arrangement of the optical markers 18, the locating system 10 may determine whether the device 22, 24 is movable or fixed and the exact type or category of device 22, 24, as well as correlate stored information with the detected type of device 22, 24.

In step 108, the position of each optical marker 18 and, consequently, the movable device 22 may be detected using the 3D sensor 26. The 3D sensor 26 may be configured to emit light and determine the distance between the 3D sensor 26 and each optical marker 18 based on the difference in time between when the light is emitted from the 3D sensor 26 and when the reflected light is received by the 3D sensor 26. The initial position data may be communicated to the controller 34. It is contemplated that the 3D sensor 26 may continually obtain initial position data for each optical marker 18, may periodically obtain initial position data, or may obtain initial position data in response to a user command.

In step 110, the controller 34 may verify or confirm the position of the additional device within the surgical suite 14. The locating system 10 may utilize the 3D sensor 26 to obtain an estimation of the position (e.g., the initial position data) of the optical markers 18 on the fixed devices 24 and other movable devices 22. The controller 34 may compare the sensed position of the optical markers 18 with stored locations for each fixed device 24.

In step 112, the position of each optical marker 18 on the selected movable device 22 may be detected and confirmed using the laser device 30. The laser device 30 may use triangulation or pulse modulation to detect a more precise or accurate position for each optical marker 18. The subsequent position data may be communicated to the controller 34. It is contemplated that the laser device 30 may continually obtain the subsequent position data for each optical marker 18, may periodically obtain subsequent position data, or may obtain subsequent position data in response to a user command.

In step 114, the subsequent position data for the additional devices, including the fixed devices 24 and the other movable devices 22, may be obtained with the laser device 30. The subsequent position data may provide confirmation of the precise position and orientation of the devices 22, 24. The laser device 30 may be utilized to confirm or verify the position of the devices 22, 24. The controller 34 may compare the subsequent position data with stored information on the position of the fixed devices 24 and the optical markers 18 on the fixed devices 24.

In step 116, the controller 34 may calculate or determine the movement path 36, the adjustment path 38, or a combination thereof based on the movable device 22 or the movable devices 22 to be moved. The controller 34 may utilize the initial and subsequent position data of the devices 22, 24 within the surgical suite 14, as well as the position of any other optical markers 18 within the surgical suite 14. The controller 34 may then determine the movement path 36 or the adjustment path 38 that allows the movable device 22 to reach the subsequent position or state and avoids collisions with other detected devices 22, 24 or objects within the surgical suite 14. Accordingly, the controller 34 is configured to determine and confirm the position of the selected movable device 22 as well as the additional devices in the surgical suite 14 to provide the movement path 36 or the adjustment path 38 that is free of the additional devices.

In step 118, the movable device 22 may be moved within the surgical suite 14 in response to the detected position and the detected type of movable device 22. The controller 34 may communicate a signal to the movable device 22, which may then send a corresponding signal to the adjustment feature 90. The movable device 22 may be moved along the movement path 36 between the initial location (e.g., a first position) and a subsequent location (e.g., a second position) within the surgical suite 14. The movement path 36 or the adjustment path 38 may be defined by the controller 34 or the control unit 66 and may be free of any other detected devices or structures within the surgical suite 14. The controller 34 may design the movement path 36 and the adjustment path 38 in response to a variety of detected data and stored data to avoid collisions between the movable device 22 and other devices and structures 22, 24 in the surgical suite 14. It is contemplated that the movable device 22 may be moved along the adjustment path 38 in a similar manner to avoid collisions. For example, The movable device 22 may be moved along the adjustment path 38 between the initial position (e.g., a first state) and a subsequent position (e.g., a second state) within the surgical suite 14.

The controller 34 may also assist in guiding the movable device 22 along the movement path 36 or the adjustment path 38. For example, the controller 34 may communicate portions of the movement path 36 or the adjustment path 38 on a continual basis as the movable device 22 is in motion. Alternatively, the controller 34 may communicate an entirety of the movement path 36 or the adjustment path 38 to the control unit 66.

In step 120, the locating assembly 42 may continue to monitor the position of the movable device 22 during motion and adjust or stop the movement of the movable device 22. The locating assembly 42 may continually monitor the position of the optical markers 18 within the surgical suite 14. The controller 34 may monitor if the movable device 22 is still on the previously determined movement path 36 or the adjustment path 38. Further, the controller 34 may determine if another object having optical markers 18 has been moved into the movement path 36 or the adjustment path 38. The controller 34 may communicate with the control unit 66 to stop the movable device 22 to avoid the potential collision. Additionally or alternatively, the controller 34 may determine a new movement path 36 or adjustment path 38 for the movable device 22.

In step 122, the laser device 30 may project the information 56 into the surgical suite 14. The type of information 56 projected may be determined based on a user input, predefined settings, etc. The laser device 30 may project the information 56 to a predefined location within the surgical suite 14 to provide the information 56 to the medical professionals. Generally, the predefined projection location provides for spatial alignment of the information 56 without significant distortion. The information 56 may relate to the patient, the various devices 22, 24 within the surgical suite 14, etc. In certain aspects, the information 56 projected by the laser device 30 may be an output relating to detected position of various devices 22, 24 and characteristics (e.g., maximum stroke, trend tilt, etc.) of the devices 22, 24. This information 56 may also be output through different user interface devices without departing from the teachings herein.

The method 100 may be performed automatically by the locating system 10, which may provide coordinated automatic movement of movable devices 22 within the surgical suite 14. In such examples, the locating system 10 may be activated through a user command or another activation signal (e.g., preparation of the surgical suite 14). Once the locating system 10 is activated, the locating system 10 may continually monitor the positions of each movable device 22 within the surgical suite 14.

Additionally or alternatively, the method 100 may be performed in response to a user command. A user, such as the medical professional or a caregiver within the surgical suite 14, can provide a user command through a user-interface to initiate the method 100. It is contemplated that the method 100 may be performed continually, periodically, sporadically, upon user command, or a combination thereof. The method 100 allows the locating system 10 to detect and register movable devices 22 and, consequently, control the movement of the movable devices 22 in a manner that avoids collisions. The method 100 may provide improved accuracy in positioning movable devices 22 within the surgical suite 22, as well as increasing flexibility of the space within the surgical suite 14. It is understood that the steps of the method 100 may be performed in any order, simultaneously and/or omitted without departing from the teachings provided herein.

Use of the present device may provide for a variety of advantages. For example, the locating system 10 obtains position data for each movable device 22 within the surgical suite 14 using the 3D sensor 26 and the laser device 30. The laser device 30 may increase the precision and accuracy of the position data. Further, the locating system 10 may be configured to control the movement of some or all of the movable devices 22 within the surgical suite 14. Also, the 3D sensor 26 may detect a type of movable device 22 and a type of fixed device 24 within the surgical suite 14. The locating system 10 may move each movable device 22 having the control unit 66 along the movement path 36 or the adjustment path 38 in response to the initial position data, the subsequent position data, the identification data, the stored data, or a combination thereof.

Additionally, for independently movable devices 22, the controller 34 may direct the movable device 22 along the movement path 36 or the adjustment path 38 to avoid collisions with other registered or detected devices and structures within the surgical suite 14. The movement path 36 provides for the movable device 22 to translate from one physical position to another physical position, and the adjustment path 38 provides for the movable device 22 to move from a first setting or state to a second setting or state. Accordingly, the locating system 10 may be used for collision monitoring of detected and registered devices and structures within the surgical suite 14. Further, the locating system 10 may provide improved accuracy and flexibility within the surgical suite 14, as well as remote or automatic coordination of the movable medical devices 22. These and other benefits or advantages may be realized and/or achieved.

The device disclosed herein is further summarized in the following paragraphs and is further characterized by combinations of any and all of the various aspects described therein.

According to an aspect of the present disclosure, a locating system for a surgical suite includes optical markers coupled to a medical device. A sensor is configured to obtain initial position data of the optical markers. A laser device is configured to obtain subsequent position data of the optical markers. A controller is configured to receive the initial position data from the sensor and the subsequent position data from the laser device. The controller is configured to determine a position of the medical device within said surgical suite and recognize a type of the medical device in response to the optical markers.

According to another aspect, a medical device includes an adjustment feature communicatively coupled to a controller. The adjustment feature is configured to adjust the medical device along at least one of a movement path and an adjustment path in response to a signal from the controller.

According to another aspect, a characteristic of a medical device is adjusted when the medical device moves along an adjustment path. The characteristic of the medical device includes at least one of a height, a rotation, a maximum stroke, a trend, and a tilt of the medical device.

According to another aspect, optical markers are disposed in a pattern on a medical device. A controller is configured to determine a type of the medical device based on the pattern.

According to another aspect, a laser device is configured to project information onto a surface within said surgical suite.

According to another aspect, information includes at least one of device movement data, device type data, obstruction data, device position data, and patient data.

According to another aspect, a controller is configured to control movement of a medical device within said surgical suite in response to initial position data and subsequent position data.

According to another aspect, a method of adjusting a device within a surgical suite includes detecting a type of a medical device within said surgical suite and determining whether the medical device is a fixed device or a movable device. A position of the medical device is determined using a sensor and at least one optical marker coupled to the medical device. At least one of a movement path and an adjustment path for the medical device is determined. The medical device is moved within said surgical suite in response to a detected position of the medical device.

According to another aspect, a step of moving a medical device includes moving the medical device along a movement path from a first position to a second position within said surgical suite.

According to another aspect, a step of moving a medical device includes moving the medical device along an adjustment path from a first state to a second state.

According to another aspect, a step of moving a medical device includes moving the medical device within said surgical suite in response to at least one of a detected type of the medical device and a triggering event.

According to another aspect, a position of the at least one optical marker, and consequently, a position of a medical device is confirmed using a laser device.

According to another aspect, a step of moving the medical device includes moving the medical device along the movement path from a first position to a second position within said surgical suite.

According to another aspect, a step of moving the medical device includes moving the medical device along the adjustment path from a first state to a second state.

According to another aspect, a step of moving the medical device includes moving the medical device within said surgical suite in response to at least one of a detected type of the medical device and a triggering event.

According to another aspect, a position of the at least one optical marker, and consequently, the position of the medical device is confirmed using a laser device.

According to another aspect, a position of additional devices is determines within said surgical suite using a sensor and an additional optical marker coupled to each additional device. The position of the additional devices within said surgical suite is determined using the laser device of the additional optical markers.

According to another aspect, a step of determining at least one of the movement path and the adjustment path includes calculating at least one of the movement path and the adjustment path to be free of the additional devices.

According to another aspect, at least one optical marker includes a plurality of optical markers arranged in a predefined pattern. A step of detecting a type of the medical device includes recognizing the predefined pattern of the plurality of optical markers coupled to the medical device.

According to another aspect, a locating system for a surgical suite includes a plurality of optical markers coupled to a medical device. A sensor is configured to obtain initial position data of the plurality of optical markers. A laser device is configured to obtain subsequent position data of the plurality of optical markers. A controller is configured to receive the initial position data from the sensor and the subsequent position data from the laser device. The controller is configured to determine a position of the medical device within said surgical suite. An adjustment feature is coupled to the medical device and is communicatively coupled to the controller. The adjustment feature is configured to adjust the medical device along at least one of a movement path and an adjustment path in response to a signal from the controller.

According to another aspect, a characteristic of a medical device is adjusted when the medical device moves along an adjustment path. The characteristic of the medical device includes at least one of a maximum stroke, a trend, and a tilt of the medical device.

According to another aspect, an adjustment feature is configured to adjust the medical device from an initial position to a subsequent position within said surgical suite when a medical device is adjusted along the movement path.

According to another aspect, a sensor is at least one of a three-dimensional sensor and a time-of-flight camera.

According to another aspect, a plurality of optical markers are arranged in a predefined pattern on a medical device. A controller is configured to recognize the predefined pattern to determine a type of the medical device.

A means for locating devices within a surgical suite includes a means for detecting coupled to a medical device. A means for measuring a distance is configured to obtain initial position data of the means for detecting. A means for confirming a measurement is configured to obtain subsequent position data of the means for detecting. A means for determining a position is configured to receive the initial position data from the means for measuring a distance and the subsequent position data from the means for confirming a measurement. The means for determining a position is configured to determine a position of the medical device within the surgical suite. The means for determining a position is configured to recognize a type of the medical device in response to the means for detecting.

Related applications, for example those listed herein, are fully incorporated by reference. Descriptions within the related applications are intended to contribute to the description of the information disclosed herein as may be relied upon by a person of ordinary skill in the art. Any changes between any of the related applications and the present disclosure are not intended to limit the description of the information disclosed herein, including the claims. Accordingly, the present application includes the description of the information disclosed herein as well as the description of the information in any or all of the related applications.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A locating system for a surgical suite, comprising:
    optical markers coupled to a medical device;
    a locating assembly configured to be coupled with a ceiling in said surgical suite, the locating assembly including:
        a time-of-flight sensor including a light source and an image sensor and configured to obtain initial position data of the optical markers and a distance between the medical device and the time-of-flight sensor; and
        a laser device including a laser light source and a detector, the laser device configured to emit light to obtain subsequent position data of each optical marker based on the initial position data, wherein the laser device is configured to utilize the initial position data to determine a direction to direct the light; and
    a controller configured to receive the initial position data from the time-of-flight sensor and the subsequent position data from the laser device, wherein the controller is configured to:
        determine a position and an orientation of the medical device within said surgical suite utilizing both the initial position data and the subsequent position data; and
        recognize a type of the medical device in response to the optical markers.

2. The locating system of claim 1, wherein the medical device includes an adjustment feature communicatively coupled to the controller, wherein the adjustment feature is configured to adjust the medical device along at least one of a movement path and an adjustment path in response to a signal from the controller.

3. The locating system of claim 2, wherein a characteristic of the medical device is adjusted when the medical device moves along the adjustment path, and wherein the characteristic of the medical device includes at least one of a height, a rotation, a maximum stroke, a trend, and a tilt of the medical device.

4. The locating system of claim 1, wherein the optical markers are disposed in a pattern on the medical device, and wherein the controller is configured to determine the type of the medical device based on the pattern.

5. The locating system of claim 1, wherein the laser device is configured to project information onto a surface within said surgical suite.

6. The locating system of claim 5, wherein the information includes at least one of device movement data, device type data, obstruction data, device position data, and patient data.

7. The locating system of claim 1, wherein the controller is configured to:
    determine at least one of a movement path and an adjustment path for the medical device prior to movement of the medical device; and
    control the movement of the medical device along the at least one of the movement path and the adjustment path within said surgical suite in response to the initial position data and the subsequent position data.

8. A method of adjusting a device within a surgical suite, comprising:
    detecting a type of a medical device within said surgical suite;
    determining whether the medical device is a fixed medical device or a movable medical device, the movable medical device having a feature for moving the movable medical device in at least one direction in response to a control signal;
    estimating a position of the movable medical device using a three-dimensional sensor and at least one optical marker coupled to the medical device;
    confirming the position of the movable medical device using a laser device and the at least one optical marker based on the position estimated by the three-dimensional sensor;
    determining an orientation of the movable medical device using the laser device and the at least one optical marker;
    determining at least one of a movement path and an adjustment path for the movable medical device prior to movement of the movable medical device; and moving the movable medical device via the feature within said surgical suite in response to a confirmed position and orientation of the medical device.

9. The method of claim 8, wherein the step of moving the movable medical device includes moving the movable medical device along the movement path from a first position to a second position within said surgical suite.

10. The method of claim 8, wherein the step of moving the movable medical device includes moving the medical device along the adjustment path from a first state to a second state.

11. The method of claim 8, wherein the step of moving the movable medical device includes moving the movable medical device within said surgical suite in response to at least one of a detected type of the movable medical device and a triggering event.

12. The method of claim 8, further comprising:
determining a position of additional devices within said surgical suite using the three-dimensional sensor and an additional optical marker coupled to each additional device; and
confirming the position of the additional devices within said surgical suite using the laser device the additional optical markers.

13. The method of claim 12, wherein the step of determining at least one of the movement path and the adjustment path includes calculating at least one of the movement path and the adjustment path to be free of the additional devices.

14. The method of claim 8, wherein the at least one optical marker includes a plurality of optical markers arranged in a predefined pattern, and wherein the step of detecting the type of the medical device includes recognizing the pattern of the plurality of optical markers coupled to the medical device.

15. A locating system for a surgical suite, comprising:
a plurality of optical markers coupled to a medical device;
a three-dimensional sensor including a light source and an image sensor and configured to obtain initial position data of the plurality of optical markers utilizing emitted light;
a laser device including a laser light source and a detector, the laser device configured to emit light to obtain subsequent position data of the plurality of optical markers, wherein the laser device is configured to utilize the initial position data to determine a direction to emit the light to obtain the subsequent position data; and
a controller configured to receive the initial position data from the sensor and the subsequent position data from the laser device, the controller configured to:
determine an estimated position of the medical device within said surgical suite based on the initial position data from the three-dimensional sensor;
adjust the laser device in response to the initial position data to emit the light toward the estimated position;
confirm a position of the medical device within said surgical suite based on the subsequent position data from the laser device; and
determine at least one of a movement path and an adjustment path for the medical device prior to movement of the medical device; and
an adjustment feature coupled to the medical device and communicatively coupled to the controller, wherein the adjustment feature is configured to adjust the medical device along the at least one of the movement path and the adjustment path in response to a control signal from the controller.

16. The locating system of claim 15, wherein a characteristic of the medical device is adjusted when the medical device moves along the adjustment path, and wherein the characteristic of the medical device includes at least one of a maximum stroke, a trend, and a tilt of the medical device.

17. The locating system of claim 15, wherein the adjustment feature is configured to adjust the medical device from an initial position to a subsequent position within said surgical suite when the medical device is adjusted along the movement path.

18. The locating system of claim 15, wherein the plurality of optical markers is arranged in a predefined pattern on the medical device, and wherein the controller is configured to recognize the predefined pattern to determine a type of the medical device.

* * * * *